(12) United States Patent
Gelfand

(10) Patent No.: US 9,849,457 B2
(45) Date of Patent: Dec. 26, 2017

(54) DUAL BARCODE LABELING FACILITATING AUTOMATED DECAPPING

(71) Applicant: Becton, Dickinson and Company, Franklin Lakes, NJ (US)

(72) Inventor: Craig A. Gelfand, Jackson, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 37 days.

(21) Appl. No.: 14/159,794

(22) Filed: Jan. 21, 2014

(65) Prior Publication Data

US 2014/0206030 A1 Jul. 24, 2014

Related U.S. Application Data

(60) Provisional application No. 61/755,118, filed on Jan. 22, 2013.

(51) Int. Cl.

| G06Q 10/00 | (2012.01) |
| B01L 3/00 | (2006.01) |
| G01N 35/00 | (2006.01) |
| G09F 3/00 | (2006.01) |
| G09F 3/02 | (2006.01) |
| G01N 35/04 | (2006.01) |

(52) U.S. Cl.
CPC .......... *B01L 3/5453* (2013.01); *B01L 3/5457* (2013.01); *G01N 35/00732* (2013.01); *G09F 3/0297* (2013.01); *B01L 2300/022* (2013.01); *G01N 2035/00782* (2013.01); *G01N 2035/0405* (2013.01); *G09F 2003/0273* (2013.01); *Y10T 436/11* (2015.01)

(58) Field of Classification Search
None
See application file for complete search history.

(56) References Cited

U.S. PATENT DOCUMENTS

| 5,019,243 A | 5/1991 | McEwen et al. |
| 5,276,315 A | 1/1994 | Surka |
| 5,401,110 A | 3/1995 | Neeley |
| 5,507,410 A | 4/1996 | Clark et al. |
| 5,921,396 A * | 7/1999 | Brown, Jr. .......... A61B 10/007 206/223 |
| 6,102,289 A | 8/2000 | Gabrielson |
| 6,428,640 B1 | 8/2002 | Stevens et al. |
| 6,550,685 B1 | 4/2003 | Kindberg |

(Continued)

FOREIGN PATENT DOCUMENTS

| CA | 2346550 A1 * 11/2002 ........... G06Q 20/342 |
| CN | 101072641 A 11/2007 |

(Continued)

*Primary Examiner* — Fateh M Obaid
(74) *Attorney, Agent, or Firm* — The Webb Law Firm

(57) ABSTRACT

A specimen collection assembly and method for detecting the same are disclosed. The specimen collection assembly includes a specimen collection container having an open top end, a closed bottom end, and a sidewall extending therebetween defining an interior adapted to receive a biological specimen. The specimen collection container also includes first indicia containing information. The assembly further includes a cap having thereon second indicia, the cap being removably engagable with the open top end of the container. The second indicia contains the same information as the first indicia.

12 Claims, 2 Drawing Sheets

(56) References Cited

U.S. PATENT DOCUMENTS

| | | |
|---|---|---|
| 6,599,476 B1 | 7/2003 | Watson et al. |
| 6,758,400 B1 | 7/2004 | Reasoner et al. |
| 2001/0021531 A1 | 9/2001 | Goldsmith |
| 2003/0039583 A1 | 2/2003 | Miller et al. |
| 2004/0215480 A1 | 10/2004 | Kadaba |
| 2005/0121528 A1 | 6/2005 | Lubow |
| 2005/0196323 A1 | 9/2005 | Itoh |
| 2005/0252973 A1 | 11/2005 | Itoh |
| 2006/0091669 A1* | 5/2006 | Wilkinson ............ B01L 3/5453 283/74 |
| 2006/0180659 A1* | 8/2006 | Loffredo ............... G06F 3/1205 235/380 |
| 2006/0213964 A1 | 9/2006 | Excoffier et al. |
| 2006/0267753 A1 | 11/2006 | Hussey et al. |
| 2007/0166198 A1* | 7/2007 | Sangha ............ A61B 10/0045 422/400 |
| 2008/0003148 A1 | 1/2008 | Dause |
| 2008/0121688 A1* | 5/2008 | Harrop ............ G06K 19/06028 235/375 |
| 2010/0111767 A1* | 5/2010 | Yonekura ............. G01N 35/026 422/65 |
| 2012/0331473 A1 | 12/2012 | You |
| 2013/0183772 A1* | 7/2013 | Fleming ............ G01N 21/8483 436/501 |

FOREIGN PATENT DOCUMENTS

| | | |
|---|---|---|
| CN | 202438333 U | 9/2012 |
| CN | 102841812 A | 12/2012 |
| DE | 3904258 A1 | 8/1990 |
| EP | 0736854 A1 | 10/1996 |
| EP | 1605396 A2 | 12/2005 |
| JP | 8329210 A | 12/1996 |
| JP | 2000098898 A | 4/2000 |
| JP | 2002082120 A | 3/2002 |
| JP | 2002259919 A | 9/2002 |
| JP | 2002318540 A | 10/2002 |
| JP | 2003112773 A | 4/2003 |

* cited by examiner

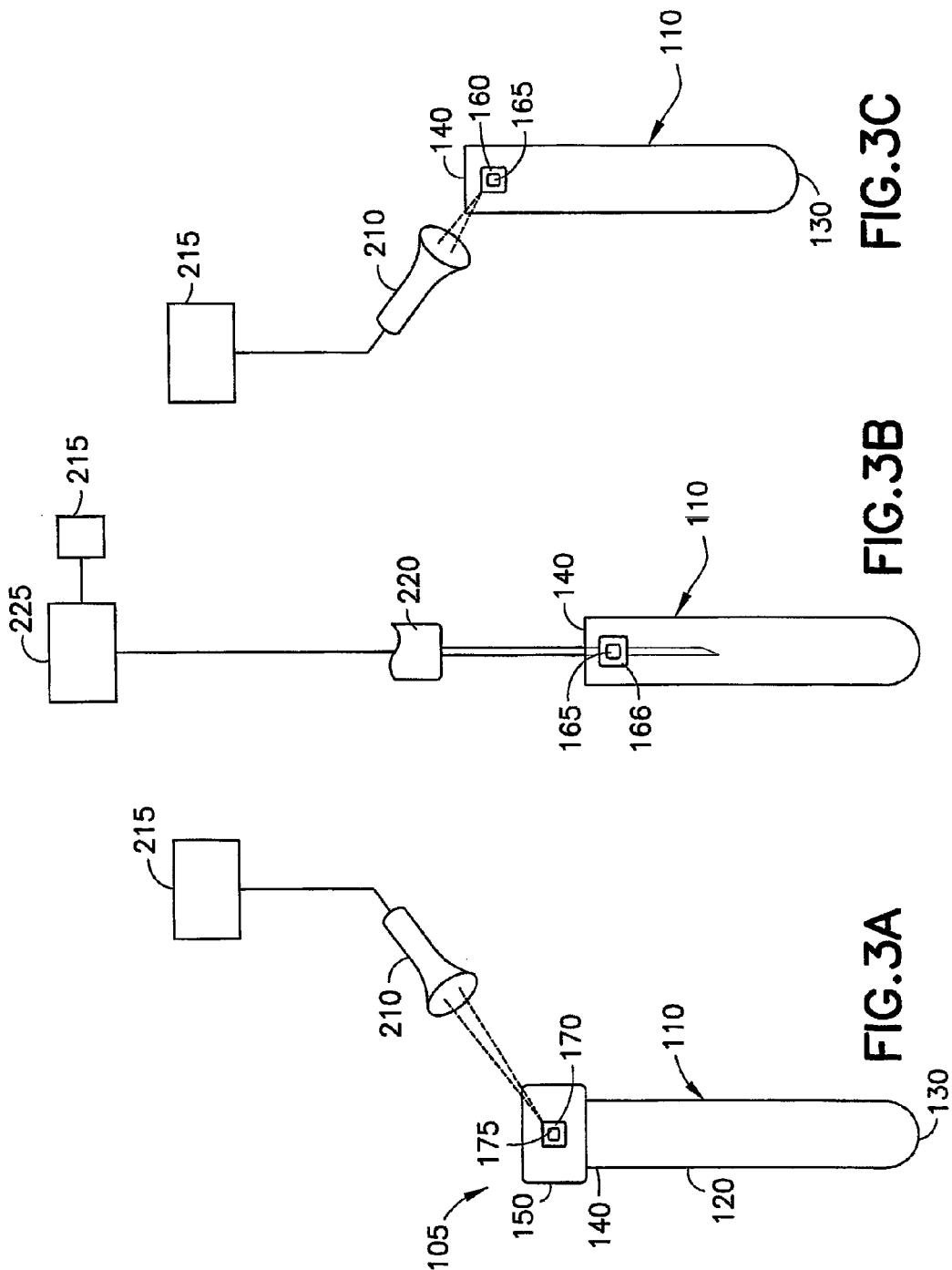

DUAL BARCODE LABELING FACILITATING AUTOMATED DECAPPING

CROSS-REFERENCE TO RELATED APPLICATION

The present application claims priority to U.S. Provisional Patent Application No. 61/755,118 filed Jan. 22, 2013, entitled "Dual Barcode Labeling Facilitating Automated Decapping", the entire disclosure of which is hereby incorporated by reference herein.

BACKGROUND OF THE INVENTION

Field of the Invention

The present invention relates to labels, labeling systems, and methods of detecting labels for use with specimen collection containers. More specifically, the present invention relates to labels, labeling systems, and methods of detecting labels for specimen collection containers that do not interfere with conventional processing and automated processing systems and that ensure accurate identification and analysis of specimens.

Description of the Related Art

Traditionally, specimen collection containers included a blank label on which a medical professional could record information relating to the patient, the sample collected, the conditions under which the sample was collected, and the analyses to be performed. More recently, specimen collection containers have been developed that include pre-printed information that indicates the additives (if any) contained in the container and the analyses for which the additives, and thus the container, are suited. This information may be provided on a label or may be directly imprinted on the container.

As part of automated clinical laboratory specimen processing, automated processing systems, such as those that de-cap and/or re-cap specimen collection containers, are typically used during specific diagnostic or evaluation testing procedures. These automated systems in many cases may damage or obscure the information printed on the specimen collection container, whether that information is provided directly on the container or on a label.

Providing information on the cap of the specimen collection container, which is not subject to the grasping and transfer mechanisms of automated processing systems, has been suggested as a solution to the problem of obscured information. However, automated processing systems typically remove the cap of the specimen collection container in order to access the sample held therein. As such, caps may become displaced, separated from their initial specimen collection container, or may be inadvertently associated with a different container, which may lead to dangerous errors in reporting results.

Accordingly, a need remains for a means for providing information relating to manufacturing conditions, manufacturing date, expiration date, specimen collection conditions, container additives, analyses to be conducted, patient identification, and the like that is reliably provided on a specimen collection container and that is less vulnerable to damage by automated processing systems, or inadvertent misplacement of caps or misidentification that may occur if caps from specimen collection assemblies are transposed.

SUMMARY OF THE INVENTION

In accordance with an embodiment of the present invention, a container assembly, such as a specimen collection assembly includes a specimen collection container having an open top end, a closed bottom end, and a sidewall extending therebetween. The open top end, closed bottom end, and sidewall define an interior of the container adapted to receive a specimen therein. The specimen collection assembly also includes a cap that is removably engagable with the open end of the specimen collection container. The specimen collection assembly also includes first and second indicia. The first indicia is disposed on at least a portion of the sidewall of the specimen collection container and the second indicia is disposed on at least a portion of the cap. The first and second indicia include the same information.

Optionally, the cap of the specimen collection assembly is opaque. In this way, when the cap is engaged with the open end of the specimen collection container, the open top end of the container is obscured from view. In certain configurations, the cap, when engaged with the open end of the specimen collection container, at least partially obscures the first indicia. In another embodiment, the cap, when engaged, fully obscures the first indicia.

The indicia may be any type of indicia, and in some embodiments are indicia that are readable by a detector. The indicia may be barcodes, for example matrix barcodes or linear barcodes. The barcodes may be displayed in either two or three dimensions. The indicia may also be of the type that does not require visible or tactile detection. For example, the indicia may be a radio frequency identification (RFID) tag. The indicia may be human-readable, machine readable, or both human-readable and machine-readable.

In certain configurations, the indicia may be disposed directly on the surface of the sidewall and cap, respectively. Alternatively, in accordance with another embodiment, the indicia may be provided on labels that are affixed to the sidewall and cap, respectively.

In accordance with another embodiment of the present invention, a method of detecting a specimen collection assembly includes providing a specimen collection assembly having a specimen collection container having an open end, a closed end, and a sidewall extending therebetween defining an interior adapted to receive a specimen, and a first indicia disposed thereon. The assembly also includes a cap engagable with the open end of the specimen collection container, the cap having a second indicia disposed thereon. The method includes detecting the second indicia, removing the cap, and detecting the first indicia. In certain embodiments the method includes providing an automated processing system including at least one detector and an analyzer, detecting the second indicia with the at least one detector, removing the cap from the specimen collection container, and detecting the first indicia with the at least one detector. In certain embodiments the method includes performing at least one analysis on the sample with the analyzer.

The indicia present on the collection container used in the method may be any type of indicia and may be human-readable, machine readable, or both human-readable and machine-readable. In such embodiments the detector may be configured to detect the indicia. The indicia may be barcodes, for example matrix barcodes or linear barcodes. The barcodes may be displayed in either two or three dimensions. The indicia may also be of the type that does not require visible or tactile detection. For example, the indicia may be a radio frequency identification (RFID) tag. The indicia may be human-readable, machine readable, or both human-readable and machine-readable.

In certain configurations, the indicia may be disposed directly on the surface of the sidewall and cap, respectively. Alternatively, in accordance with another embodiment, the indicia may be provided on labels that are affixed to the sidewall and cap, respectively.

In another embodiment of the present invention, a method of labeling a specimen collection assembly is provided, the method including the steps of providing a specimen collection container having an open top end, a closed bottom end, and a sidewall extending therebetween defining an interior adapted for receiving a specimen therein, providing a cap removably engagable with the open top end of the specimen collection container, applying a first indicia to the specimen collection container, applying a second indicia to the cap, and comparing the first indicia to the second indicia to confirm that they are the same indicia. In certain embodiments, the indicia are machine-readable indicia. In embodiments, the indicia are present on labels that are applied to the specimen collection container and the cap.

BRIEF DESCRIPTION OF THE DRAWINGS

FIG. 3A is a front perspective view of a first detection step in an embodiment of the method of the present invention.

FIG. 3B is a front perspective view of an analysis step in an embodiment of the method of the present invention.

FIG. 3C is a front perspective view of a second detection step in an embodiment of the method of the present invention.

DETAILED DESCRIPTION OF THE EMBODIMENTS

Figures 1, 2:
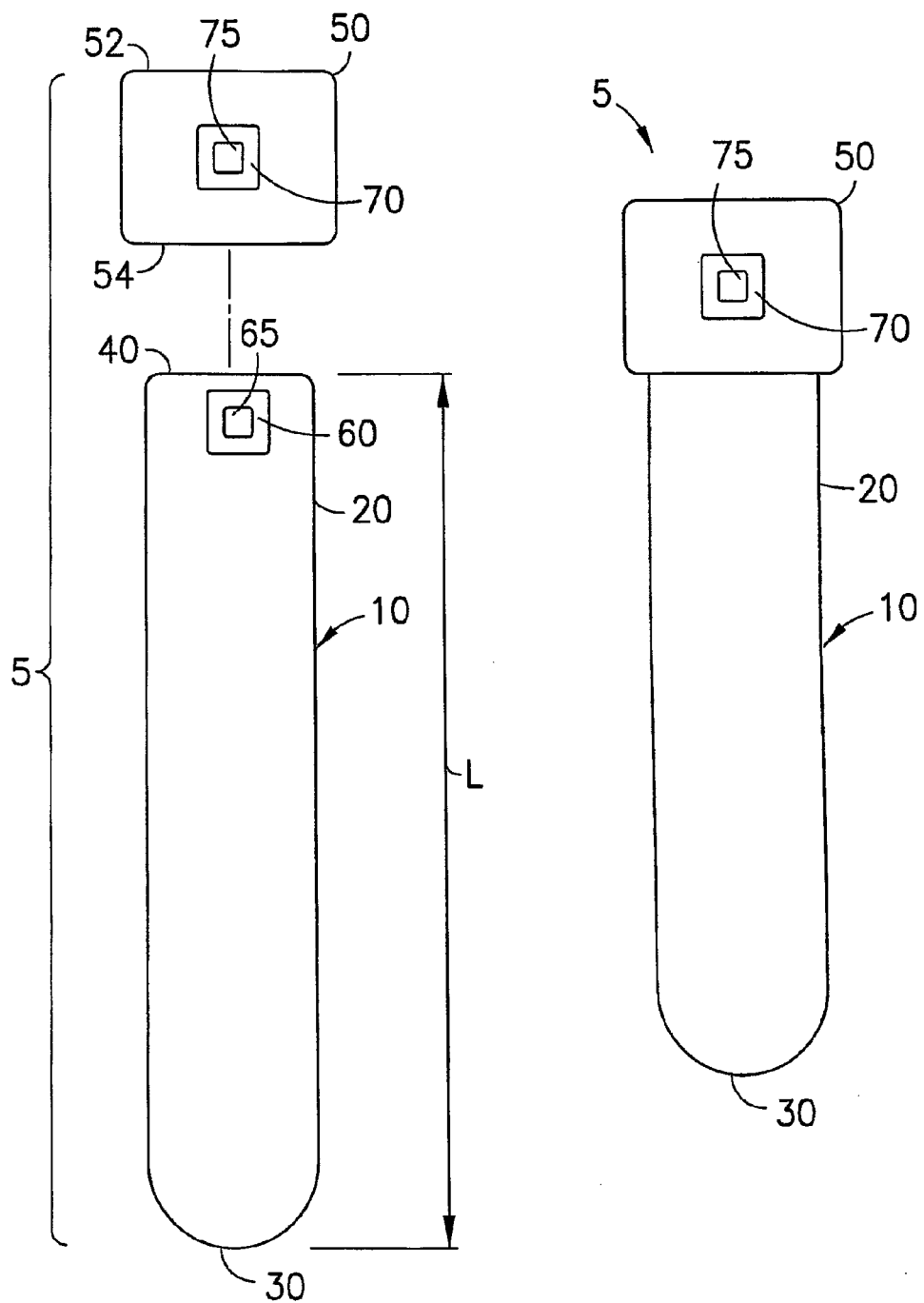
FIG. 1 is a front perspective view of a specimen collection assembly including a specimen collection container having the cap disengaged therefrom in accordance with an embodiment of the present invention.
FIG. 2 is a front perspective view of a specimen collection assembly including a specimen collection container having the cap engaged therewith in accordance with an embodiment of the present invention.

For purposes of the description hereinafter, spatial orientation terms, if used, shall relate to the referenced embodiment, as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The present invention is directed to a specimen collection assembly and method for detecting such a specimen collection assembly. The specimen collection assembly has indicia provided in at least two different locations of the collection assembly, for example, on the cap of the specimen collection container and on the specimen collection container body itself. The indicia is provided such that information about the patient, specimen, the container itself including part number, lot number, manufacture date, expiration date of any reagents or additives included therein, and/or analyses to be conducted may be verified during manual processing or by an automated processing system, thereby reducing errors and allowing for more accurate analysis and reporting of results.

A method of detecting the specimen collection assembly includes providing a specimen collection assembly having at least two indicia, wherein at least one of the indicia is on the cap of the assembly, and detecting the indicia. In further embodiments the method also includes providing an automated processing system having at least one detector for detecting indicia. In further non-limiting embodiments, the detector is in communication with a control unit having at least one processor and at least one analyzer. In such non-limiting embodiments, the at least one detector detects one of the indicia on the specimen container located on the cap, removes the cap, performs analyses as needed, and detects, with the at least one detector, another indicia on the specimen container body.

With reference to FIG. 1, an embodiment of the present invention is shown. The specimen collection assembly 5 includes a specimen collection container 10. The specimen collection container 10 may include an open top end 40, a closed bottom end 30, and a sidewall 20 extending therebetween. The open top end 40, closed bottom end 30, and sidewall 20 define an interior adapted to receive a biological specimen, for example blood, therein. The interior of the collection container 10 includes an inside diameter extending substantially uniformly from the open top end 40 to a location substantially adjacent the closed bottom end 30 along the longitudinal axis of the collection container 10, as shown in FIG. 1.

The specimen collection container 10 may be a single-walled container formed of one or more than one of the following representative materials: glass, acrylic polymers and copolymers, including acrylonitrile-butadiene-styrene (ABS), styrene-acrylonitrile (SAN), ethylene vinyl alcohol (EVA), polyesters, polyethylene terephthalate (PET), polyethylene terephthalate glycol (PETG), polyethylene terephthalate naphthalene (PETN), polyethylene naphthalene (PEN), engineered thermoplastics, including polycarbonate and blends thereof, polyolefins including polyethylene, polypropylene and copolymers thereof, cyclic olefin copolymers and chloro- and fluoro-polymers including polyvinylidene chloride (PVDC), polyvinylidene fluoride (PVDF), polyvinyl fluoride (PVF), and chlorotrifluoroethylene (CTFE or ACLAR) or combinations thereof. The collection container 10 can include a single wall or multiple wall configurations. Additionally, the collection container 10 may be constructed in any practical size for obtaining an appropriate biological sample. For example, the collection container 10 may be of a size similar to conventional large volume tubes, small volume tubes, or microvolume tubes, as is known in the art. In one particular embodiment, the collection container 10 may be a standard 10 ml evacuated blood collection tube, as is also known in the art. Specifically, the collection container 10 may be a sample collection tube, such as a proteomics, molecular diagnostics, chemistry sample tube, blood, or other bodily fluid collection tube, coagulation sample tube, hematology sample tube, and the like. In a non-limiting embodiment, the specimen collection container 10 is a Vacutainer® manufactured by Becton, Dickinson and Company. In a further non-limiting embodiment, the specimen collection container 10 is a Microtainer® manufactured by Becton, Dickinson and Company.

In other configurations, the specimen collection container 10 may include a tube-in-tube configuration in which a second specimen collection container is disposed within the first container interior. The inner and outer containers may be made of the same or different materials, depending on sample to be collected or stored and analyses to be conducted. Like the specimen collection container 10, a second specimen collection container may include a closed bottom end, an open top end, and a sidewall extending therebetween defining a second container interior. The open top end of the second specimen collection container may be joined or otherwise secured with the open top end of the specimen collection container 10, such that introduction of a specimen into the specimen collection container 10 also introduces the specimen into the second container interior. A closure may cover the open top end 40 of the specimen collection container 10 and the open top end of the second specimen collection container.

In one embodiment, the collection container 10 may contain additional additives as required for particular testing procedures, such as, without limitation, preservatives, blood anticoagulants, microbiocides, additives to stabilize proteins, nucleic acids chemicals, biochemicals, or cells that comprise the sample being collected, microbial growth enhancing agents, lysis reagents, sodium citrate, tri-potassium ethylenediamine tetra-acetate ($K_3$ EDTA), heparin, lithium heparin, phenol, phenol/chloroform mixtures, alcohols, aldehydes, ketones, organic acids, salts of organic acids, alkali metal salts of halides, fluorescent dyes, antibodies, binding agents, and the like. Lysis reagents may be used to break down red blood cells for easier separation of microorganisms, as is known in the art. Such additives may be in particle or liquid form and may be sprayed onto the sidewall 20 of the collection container 10 or located at the closed bottom end 30 of the collection container 10. In further embodiments, the collection container 10 may include one or more density gradient separator elements. In certain non-limiting embodiments, the one or more separator elements are mechanical separators, gels, or both. In some non-limiting embodiments, the separator gel is a thixotropic gel.

With continuing reference to FIG. 1, the open top end 40 of collection container 10 is structured to at least partially receive a cap or closure 50 therein to form a liquid impermeable seal. The cap 50 includes a top end 52 and a bottom end 54 that may be at least partially received within the collection container 10.

In one embodiment, portions of the cap 50 adjacent the open top end 40 define a maximum outer diameter which exceeds the inside diameter of the collection container 10. In such an embodiment, portions of the cap 50 extending downwardly from the bottom end 54 may taper from a minor diameter which is approximately equal to, or slightly less than, the inside diameter of the collection container 10 to a major diameter that is greater than the inside diameter of the collection container 10 at the top end 52. Thus, in such an embodiment, the bottom end 54 of the cap 50 may be urged into a portion of the collection container 10 adjacent the open top end 40. The inherent resiliency of cap 50 can insure a sealing engagement with the interior of the sidewall 20 of the collection container 10.

In another embodiment, the cap 50 is polymeric and includes a pierceable resealable septum (not shown) penetrable by a needle cannula (not shown). In one embodiment, the cap 50 can be formed of a unitarily molded elastomeric material, having any suitable size and dimensions to provide sealing engagement with the collection container 10. Optionally, the cap 50 may be at least partially surrounded by a shield, such as a Hemogard® Shield commercially available from Becton, Dickinson and Company.

The cap 50 may be engagable with the open top end 40 of the specimen collection container 10 by any suitable means, including but not limited to interference fit or by threaded engagement of threads (not shown) on cap 50 with threads (not shown) adjacent the open top end 40 of the specimen collection container 10. In non-limiting embodiments, the cap 50 is opaque, such that when the cap 50 is engaged with the open top end 40 of the specimen collection container 10, the cap 50 at least partially obscures at least one view of the open top end 40 of the specimen collection container 10 and at least a portion of the sidewall 20 adjacent to the open top end 40. In other non-limiting embodiments, when the cap 50 is engaged with the open top end 40 of the specimen collection container 10, the cap 50 fully obscures at least one view of the open top end 40 and at least a portion of the sidewall 20 adjacent thereto.

The specimen collection container 10 of the present invention may include at least one label 60 including at least one indicia 65. The label 60 may be adapted for affixation to the specimen collection container 10 by any suitable means, including by adhesive securement. The label may be opaque or light-transmissive, or may be any combination thereof. A light-transmissive label may be translucent, transparent, or substantially clear. In non-limiting embodiments, the label 60 with indicia 65 is affixed to the specimen collection container 10 during assembly thereof.

The cap 50 of the specimen collection assembly 5 of the present invention additionally may include at least one label 70 with at least one indicia 75. Label 70 is adapted for affixation to the cap 50 by any suitable means, including by adhesive securement, and may be affixed during assembly of the specimen container assembly. In certain non-limiting embodiments, the cap is a Hemogard™ closure manufactured by Becton, Dickinson and Company.

The indicia 65, 75 may be present directly on specimen collection container 10 and cap 50, respectively, may be present on labels 60, 70, respectively, or may be present on both and are preferably the same type of indicia for reduced cost associated with an automated processing system for analyzing the biological specimen held within specimen collection container 10. Indicia 65, 75 may be any suitable type of indicia capable of being detected by an automated detector, such as, without limitation, a matrix barcode, an RFID tag, and/or a liner barcode. The indicia may be a one-dimensional, two-dimensional, or three-dimensional optical barcode. In one embodiment, the indicia are two-dimensional data matrix barcodes. This type of indicia may be particularly useful because of its ability to provide information when affixed to small items, for example the cap 50 of specimen collection assembly 5.

The indicia 65, 75 may comprise any type of information that may be useful in the collection and analysis of biological samples. For example, and without limitation, the indicia may include information about the manufacturing conditions, including location, serial number, lot number, manufacturing date, expiration date, and catalog number, or information required in product labeling standards such as Global Trade Identification Number (GTIN) which may embody many of these listed attributes. In other embodiments, indicia 65, 75 may also include information concerning additives to the tube, such as without limitation EDTA, including but not limited to concentrations of additives and reagents, source of additives and reagents, and expiration date of additives and reagents, which may relate to the particular analytes and/or analyses for which the container assembly is suited. Each indicium contains the same information, which allows for simple identification and confirmation of identification, for example by an automated processing system. Additionally, the indicia allow accurate identification of a tube which has already been de-capped by manual or automated process.

With reference to FIG. 2, an embodiment of the container assembly of FIG. 1 is depicted with the cap 50 engaged with the open end 40 of the specimen collection container 10. As may be seen, in this non-limiting embodiment, the opaque cap 50 when engaged obscures view of the open end 40 of the specimen collection container 10. This obscuring by cap 50 also obscures, at least partially, a view of label 60 including indicia 65. In this way, label 60 including indicia 65 may be protected when the cap 50 is engaged, for example during packaging, transport, and the like. The presence of indicia 65 in a manner such that it is concealed by cap 50 also protects indicia 65 from damage associated with normal handling and use during collection, transport, and/or storage of samples, as well as from overlabeling that may occur in the course of collection, transport, and/or storage of samples. While label 70 on cap 50 may be damaged during the normal course of handling, label 60 including indicia 65 is safely concealed from exposure to damage.

The specimen collection assembly 5 of the present invention may be useful for collection and storage of any biological specimen such as blood, serum, plasma, saliva, urine, bile, cerebrospinal fluid, or the like. The specimen may be introduced into the interior of the collection container 10 by any suitable means. For example, and without limitation, a clinician, nurse, or other medical professional may de-cap the assembly 5 by removing cap 50, transferring specimen to the interior of the collection container 10, and re-capping the assembly 5 by engaging cap 50 with the open top end 40 of the container 10 by any appropriate means, such as interference fit or threaded engagement.

In embodiments in which the cap 50 includes a pierceable septum, the clinician, nurse, or other medical professional may introduce specimen into the interior of the collection container 10 by piercing the septum with a needle, syringe, cannula, or other similar implement and expelling or providing the specimen therein.

By having indicia located on at least two portions of a specimen collection assembly 5, the assembly of the present invention is advantageous for use in automated processing systems. For example, if indicia were located only on the cap 50, an automated processing system may scan the indicia 75 on the cap 50, remove the cap for analyses, and then be unable to confirm the identity of the specimen collection container and the specimen held therein at a later time.

In addition to the various embodiments of the specimen collection assembly disclosed herein, additionally provided are methods of detecting a specimen collection assembly. The method includes providing a specimen collection assembly 5 having a specimen collection container 10 having an open top end 40, a closed bottom end 30, and a sidewall 20 extending therebetween, the specimen collection container 10 being adapted to receive a specimen therein. The specimen collection container 10 includes at least one label 60, having thereon at least one indicia 65. The specimen collection assembly also includes a cap 50 having at least one label 70 thereon, the label containing at least one indicia 75. The indicia may be human-readable and/or machine-readable and may contain information concerning, without limitation, the identity and type of sample, proper handling protocols, the intended testing procedure, any special considerations based on the type of sample to be held, the type of reagent or additive included, or the type of testing to be performed, collection container dimensions and features, and the like. The method further includes detecting the second indicia 75, removing the cap 50 from the collection assembly 5, and detecting the first indicia 65. In further embodiments, the method includes performing at least one analysis on a sample in the collection container. In further embodiments the detection is performed automatically, a non-limiting embodiment of which is depicted in FIGS. 3A-3C.

With reference to FIG. 3A, in an embodiment of the present invention, a method of detecting a specimen collection assembly includes providing a specimen collection assembly 105 having a specimen collection container 110 having an open top end 140, a closed bottom end 130, and a sidewall 120 extending therebetween, the specimen collection container 110 being adapted to receive a specimen therein. The specimen collection container 110 includes at least one label 160, as shown in FIG. 3B, having thereon at least one indicia 165, as also shown in FIG. 3B. The specimen collection assembly also includes a cap 150 having at least one label 170 thereon, the label containing at least one indicia 175.

Continuing with reference to FIG. 3A, the specimen collection assembly 105 may be used in an automated processing system, for example and without limitation, the Innova® system manufactured by Becton, Dickinson and Company, the processing system having at least one detector 210. In the system, the detector 210 is in communication with at least one control unit 215 having at least one processor (not shown). The at least one detector 210 detects indicia 175 on label 170 affixed to cap 150 as described above, to identify, without limitation, the identity and type of sample, proper handling protocols, the intended testing procedure, any special considerations based on the type of sample to be held, the type of reagent or additive included, or the type of testing to be performed, collection container dimensions and features, and the like. For example, in non-limiting embodiments, the indicia will provide information to the detector 210 that the collection container 110 contains therein a separator, and thus that any analysis needle to be inserted cannot be inserted past a certain depth. In certain configurations, the automated processing system is capable of removing cap 150. The cap 150 may be retained by the automated processing system or it may be discarded. In a non-limiting embodiment in which the collection assembly 5 undergoes automated processing, indicia 165, 175 may include machine-readable indicia.

With reference to FIG. 3B, the control unit 215 further includes an analyzer 225. In use, the automated processing system may remove specimen for analysis by analyzer 225 by any suitable means, for example and without limitation, with a needle, probe, or pipette 220, to analyze the biological specimen held within specimen collection container 110. In certain embodiments, the specimen may remain within collection container 110 and be analyzed by optical means or through vaporization. In embodiments in which the specimen is extracted from collection container 110, the specimen may be extracted by needle, probe, or pipette 220 by vacuum or suction and transferred to analyzer 225 for any suitable analysis.

With reference to FIGS. 3A and 3B, the at least one detector 210, in communication with control unit 215, may transmit information concerning the collection assembly 105 to the control unit 215. The control unit 215 may then instruct analyzer 225 accordingly by transmitting to the analyzer 225 the type of specimen collection container 110 that has been detected as well as other information including, but not limited to, the identity and type of sample, proper handling protocols, the intended testing procedure, any special considerations based on the type of sample to be held, the type of reagent or additive included, or the type of testing to be performed, collection container dimensions and features, and the like. It is noted herein that the detector 210 may detect indicia present on the label 160 of the collection container 110, as verification of the intended testing procedure after de-capping.

With regard to FIG. 3C, after the analysis or analyses are conducted on the specimen within collection container 110, the at least one detector 210 detects the indicia 165 present on label 160 on the specimen collection container 110. As the at least one detector 210 is in communication with control unit 215 having at least one processor (not shown), the control unit 215 is configured to compare the information obtained from indicia 175 on cap 150 and the information obtained from indicia 165 on specimen collection container 110 to determine the identity of the collection assembly, including information concerning the sample, proper handling protocols, the intended testing procedure, any special considerations based on the type of sample to be held, the type of reagent or additive included, or the type of testing to be performed, collection container dimensions and features, and the like, and provide confirmation of the same.

Also provided herein are methods of labeling a specimen collection container. The method includes the steps of providing a specimen collection container 10 having an open top end 40, a closed bottom end 30, and a sidewall 20 extending therebetween defining an interior adapted for receiving a specimen therein. The method also includes providing a cap 50 removably engagable with the open top end 40 of the specimen collection container 10. A first indicia 65 is applied to the specimen collection container 10. The indicia may be provided directly on the specimen collection container 10, may be provided on a label 60, or both. The method also includes applying a second indicia 75 to the cap 50, the second indicia 75 may be provided directly on the cap 50, on a label 70, or both. The method also includes comparing the first indicia 65 to the second indicia 75 to confirm that they are the same indicia. In certain embodiments, the indicia 65, 75 are machine-readable indicia.

While several embodiments of a specimen collection assembly and method for detecting a specimen collection assembly have been described in the foregoing detailed description, those skilled in the art may make modifications and alterations to these embodiments without departing from the scope and spirit of the invention. Accordingly, the foregoing description is intended to be illustrative rather than restrictive.

What is claimed is:

1. A specimen collection assembly comprising:
   a specimen collection container having an open top end, a closed bottom end, and a sidewall extending therebetween defining an interior adapted for receiving a specimen therein;
   a cap removably engagable with the open top end of the specimen collection container;
   a first label disposed on the sidewall of the specimen collection container;
   a second label disposed on a portion of the cap, wherein a first indicia comprising information is provided on the first label, wherein a second indicia comprising the same information as the first indicia is provided on the second label,
   wherein the first indicia and the second indicia comprise at least one of a matrix barcode, RFID tag, or linear barcode, and
   wherein the cap, when engaged with the open top end of the specimen collection container, at least partially obscures the first label disposed on the sidewall of the specimen collection container.

2. The specimen collection assembly of claim 1, wherein the first indicia and the second indicia are identical.

3. The specimen collection assembly of claim 1, wherein the cap is opaque.

4. The specimen collection assembly of claim 1, wherein the cap, when engaged with the open top end of the specimen collection container, fully obscures the first label disposed on the sidewall of the specimen collection container.

5. The specimen collection assembly of claim 1, wherein the first indicia and the second indicia comprise at least one of an optical 1D, 2D, or 3D barcode.

6. The specimen collection assembly of claim 1, wherein the first and second indicia are machine-readable indicia.

7. A specimen collection assembly comprising:
   a specimen collection container having an open top end, a closed bottom end, and a sidewall extending therebetween defining an interior adapted for receiving a specimen therein;
   a cap removably engagable with the open top end of the specimen collection container;
   a first label disposed on the sidewall of the specimen collection container;
   a second label disposed on a portion of the cap, wherein a first two-dimensional matrix barcode comprising information is provided on the first label, wherein a second two-dimensional matrix barcode comprising the same information as the first two-dimensional matrix barcode is provided on the second label, and
   wherein the cap, when engaged with the open top end of the specimen collection container, at least partially obscures the first label disposed on the sidewall of the specimen collection container.

8. The specimen collection assembly of claim 7, wherein the cap is opaque.

9. The specimen collection assembly of claim 7, wherein the cap, when engaged with the open top end of the specimen collection container, fully obscures the first label disposed on the sidewall of the specimen collection container.

10. The specimen collection assembly of claim 1, wherein the first label and the second label are a combination of opaque and light-transmissive.

11. The specimen collection assembly of claim 1, wherein the first indicia is further directly imprinted on the specimen collection container, wherein the second indicia comprising the same information as the first indicia is further directly imprinted on the cap.

12. The specimen collection assembly of claim 1, wherein the cap, when engaged with the open top end of the specimen collection container, fully obscures the first indicia provided on the first label.

* * * * *